United States Patent [19]
Riebl et al.

[11] Patent Number: 5,947,728
[45] Date of Patent: Sep. 7, 1999

[54] DENTAL APPLICATOR

[75] Inventors: Ronald K. Riebl, North Bellmore; Douglas K. Riebl; Gary K. Riebl, both of Massapequa Park, all of N.Y.

[73] Assignee: Arnel, Inc., Hempstead, N.Y.

[21] Appl. No.: 09/070,496

[22] Filed: Apr. 30, 1998

Related U.S. Application Data

[60] Provisional application No. 60/062,479, Oct. 17, 1997.

[51] Int. Cl.$^6$ .................................................. A61C 5/04
[52] U.S. Cl. ............................................. 433/90; 433/164
[58] Field of Search .............................. 433/90, 164, 83, 433/89, 80

[56] References Cited

U.S. PATENT DOCUMENTS

| | | | |
|---|---|---|---|
| 532,720 | 1/1895 | Dennis | 433/164 |
| 2,903,794 | 9/1959 | Carafagni . | |
| 3,724,076 | 4/1973 | Schmitz | 433/90 |
| 3,735,492 | 5/1973 | Karter et al. | 433/90 |
| 4,218,215 | 8/1980 | Lancellotti . | |
| 4,273,534 | 6/1981 | Seid | 433/164 |
| 4,306,863 | 12/1981 | Law et al. . | |
| 4,306,864 | 12/1981 | Law et al. . | |
| 4,355,976 | 10/1982 | Berner . | |
| 4,515,563 | 5/1985 | Dungill . | |
| 4,673,353 | 6/1987 | Nevin | 433/90 |
| 4,768,955 | 9/1988 | Hirdes . | |
| 5,098,292 | 3/1992 | Lazarof . | |
| 5,118,297 | 6/1992 | Johnson | 433/224 |
| 5,580,245 | 12/1996 | Nevin | 433/80 |
| 5,651,397 | 7/1997 | Black et al. | 141/18 |
| 5,743,431 | 4/1998 | Brattesani | 433/90 |

FOREIGN PATENT DOCUMENTS

| | | | |
|---|---|---|---|
| 2269105 | 2/1994 | United Kingdom | 433/164 |

*Primary Examiner*—Ralph A. Lewis
*Attorney, Agent, or Firm*—Dilworth & Barrese

[57] ABSTRACT

A dental applicator for applying amalgam or other filling material to a tooth is provided, in which a plunger is arranged to reciprocate into and out of a barrel to thereby eject and administer the amalgam or filling material. The barrel and/or plunger are fabricated from plastic and/or metal or metallic material provided with a coating, to inhibit or totally prevent amalgam residue from solidifying and adhering to the barrel or plunger.

21 Claims, 4 Drawing Sheets

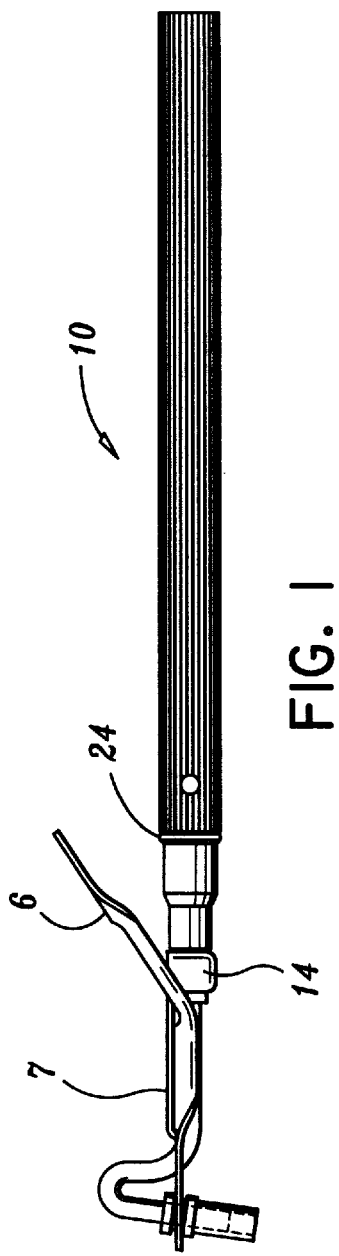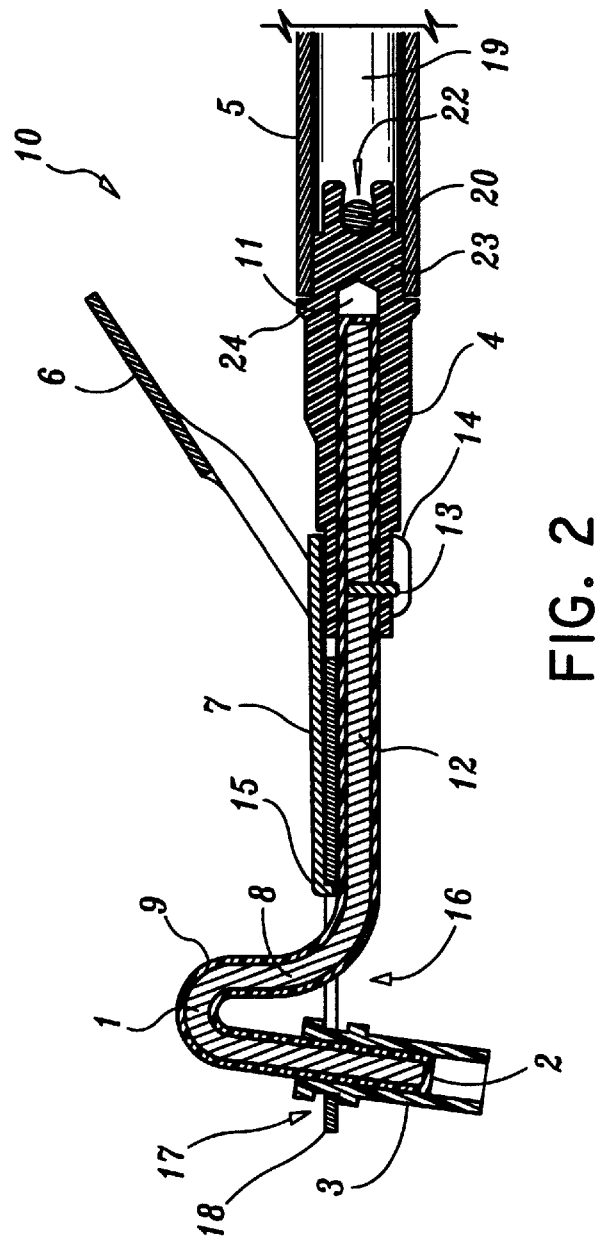

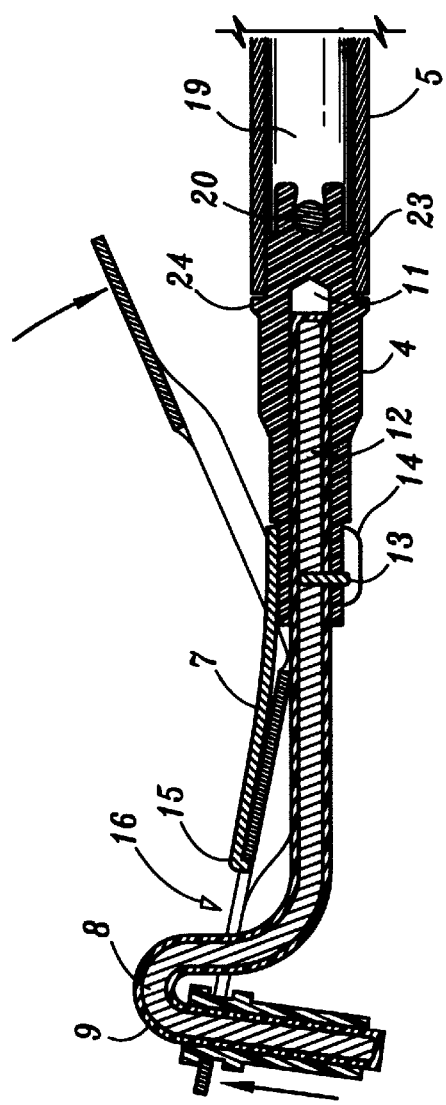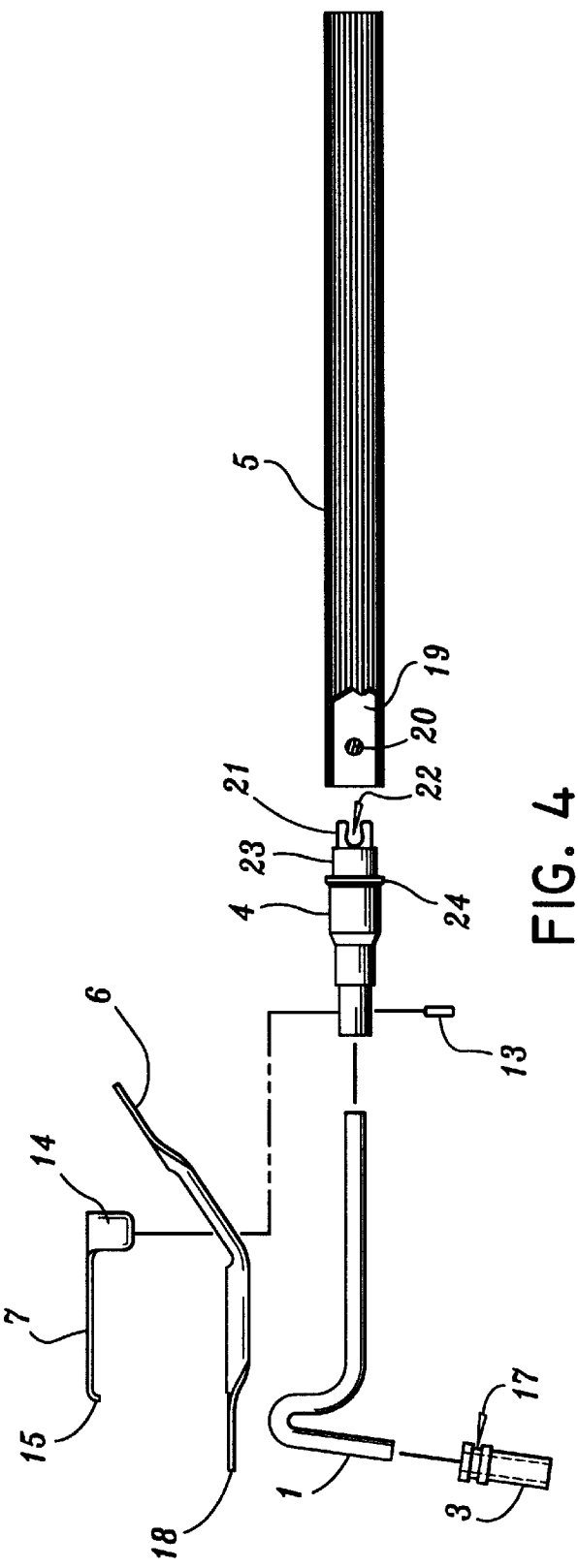

DENTAL APPLICATOR

CROSS-REFERENCE TO RELATED APPLICATION

The application claims priority from co-pending provisional application No. 60/062,479, filed Oct. 17, 1997, the contents of which are incorporated by reference herein.

BACKGROUND OF THE INVENTION

The present invention is directed to a dental applicator for applying amalgam or other filling material to teeth. More particularly, the present invention is directed to a dental applicator which can be repeatedly used without any danger of permanent clogging by hardened amalgam or filling material and which, in a preferred embodiment, comprises an amalgam dispenser which can be removed from a handle, e.g., for cleaning, replacement or alternative size combinations.

Various types of lever-activated dental amalgam applicators are known, as exemplified by U.S. Pat. No. 5,580,245 to Nevin, U.S. Pat. No. 4,355,976 to Bemer, U.S. Pat. No. 4,273,534 to Seid, U.S. Pat. No. 4,306,864 to Law et al., U.S. Pat. No. 4,673,353 to Nevin and U.S. Pat. No. 3,735,492 to Karter et al. For example, U.S. Pat. No. 4,673,353 to Nevin discloses a lever-operated applicator 10 for a light-curable dental composition in which a hollow receptacle 50 is coupled to the lever 30 and elevated by depressing the lever arm 34 (column 3, lines 47–54). The receptacle is formed from inert metal or opaque plastic (column 3, lines 58–59) while the plunger 18 which extends through the receptacle cavity can be made of any conventional clear plastic such as methacrylic acid and polymer, methylmethacrylate polymer, polycarbonate or polystyrene (column 3, lines 64–67). Preferably, a clear solid plastic core 60 forming plunger 18 is surrounded by an inert metal or plastic coating (column 3, lines 67-column 4, line 17). U.S. Pat. No. 4,273,534 to Seid discloses an amalgam carrier and dispenser having a terminal end surface 16 of a plunger 10 formed of especially hard metallic material to resist abrasion effect.

Solidificator and clogging of amalgam in the receptacle or barrel of such lever-actuated dental amalgam applicators has been a significant problem encountered by dentists. Generally, amalgam is applied onto a tooth while at room temperature, e.g., about 68° F. to about 70° F., i.e., while in malleable condition. However, because amalgam is administered under ambient temperature of about 75–80° F. (or even cooler if a dental office is air conditioned), amalgam begins to solidify immediately upon receipt within the lever-actuated barrel. Therefore, after repeated application, solidified amalgam builds upon interior surfaces of the cylindrical barrel, interfering with proper administration of amalgam filling into a tooth. Eventually, the entire barrel becomes totally clogged with solidified amalgam so that the entire amalgam applicator is rendered useless and must be discarded, handle and all.

Attempts have been made to create amalgam applicators with removable tips, e.g., U.S. Pat. No. 3,735,492 to Karter et al., so that once a tip becomes clogged, it can be removed from the amalgam carrier and replaced by a clean tip. However, such previous designs have proven cumbersome if not totally difficult to implement and furthermore do not solve the problem of initially preventing amalgam from adhering inside the lever-activated barrel.

Accordingly, it is an object of the present invention to improve dispensing and dispersing of dental amalgam or other filling material onto a tooth.

It is a more specific object of the present invention to inhibit or totally prevent accumulation of hardened amalgam or filling material within a lever-activated barrel of a dental amalgam carrier upon repeated actuation.

It is a further object of the present invention to provide a dental amalgam or filling applicator which can be effectively cleaned and re-used and/or having individual parts thereof which can be cleaned and re-used, such as a separable amalgam carrier and handle.

Further objects of the present invention will become apparent from the description herein.

SUMMARY OF THE INVENTION

These and other objects are attained by the present invention which is directed to a dental applicator for dispensing amalgam and other filling material such as condensable resin or composite resin and comprising a barrel and a plunger arranged to reciprocate into and out of the barrel. The barrel and/or plunger are fabricated from plastic or metal/metallic material provided with a coating thereon. In a preferred embodiment, the applicator is lever-activated, i.e., by pivotally mounting the barrel to reciprocate the same by pressing and releasing a lever.

The applicator of the present invention permits dental amalgam or other filling material to be reliably dispensed therefrom over repeated usage, and with minimal clogging/solidification of amalgam or filling residue within the barrel. Additionally, because of the particular combination of plastic and coated metal/metallic material for the plunger and barrel, it is extremely easy to remove the amalgam from the applicator, e.g., by brushing and/or sterilizing the components. For example, unwanted amalgam residue can simply be removed by wiping the applicator with a cotton swab dabbed with isopropyl alcohol. Furthermore, in a preferred embodiment, the applicator tip, including the lever-activated barrel and plunger, can be removed from the handle for cleaning and immediately substituted with a new applicator tip which can be easily secured to the handle for appropriate use.

When the inventive applicator is used to dispense condensable resin, any metallic streaking upon the dispensed resin is automatically eliminated, thus both improving dispensing and preventing unwanted contamination of the ultimate filling material.

BRIEF DESCRIPTION OF THE DRAWINGS

The present invention will be described in further detail with reference to the accompanying drawings, in which:

FIG. 1 is a right elevational view of a dental applicator in accordance with the present invention;

FIG. 2 is a sectional view of a front end portion of the applicator shown in FIG. 1;

FIG. 3 is a schematic sectional view, similar to FIG. 2, and illustrating operation of the dental applicator in accordance with the present invention;

FIG. 4 is an exploded view of the dental applicator shown in FIG. 1 and illustrating assembly of the various component parts;

DESCRIPTION OF THE PREFERRED EMBODIMENTS

Figure 5:
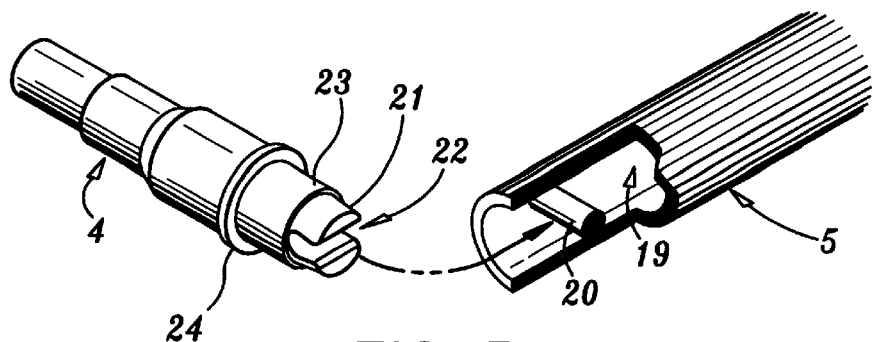
FIG. 5 is a schematic perspective view illustrating assembly of one embodiment of the dental applicator in accordance with the present invention.

Reference will be made to the accompanying drawings in which similar components are denoted with prime (') symbols.

As illustrated in the figures, e.g., FIGS. 1–4, the dental applicator 10 of the present invention comprises a handle 5, a plunger or hook 1 mounted upon the handle 5 and a barrel 3 pivotally mounted upon the plunger 1. More particularly, plunger 1 is fixed upon base 4 which is, in turn, removably mounted upon handle 5 as illustrated in FIG. 4 and as described further infra.

The barrel 3 is pivotally mounted upon the base 4 through a lever 6 and spring 7, such as a leaf spring. In the illustrated embodiment, the barrel 3 is manufactured from plastic while the plunger 1 is manufactured from metal or metallic material 8 and provided with a separate coating 9. The combination of a plastic barrel 3 with a coated metal/metallic plunger, has proven quite effective in inhibiting and even totally preventing accumulation of solidified amalgam/filling material residue within the barrel 3 upon repeated applications by a dentist. It is pointed out that the entire plunger 1 is coated, not just the tip portion thereof contacting a tooth surface, thus preventing unwanted adherence of amalgam over the entire surface thereof, especially the portion extending through the barrel 3. At the same time, ejection/administration of the entire amalgam content contained within the barrel 3 is ensured; in this regard, provision of the plastic barrel 3 in combination with the coated 9 metal/metallic plunger 8 does not sacrifice touch and control by a dentist, critical for proper lever actuation and administration of amalgam.

In other words, a dentist who has been previously trained, e.g., with an all metal applicator comprising both a metal barrel and metal plunger (conventionally available in the art) or even an applicator comprising a plastic barrel about a metal plunger, can immediately adapt to handling the inventive applicator 10 without any loss of dexterity, control, reliance and will thereby be assured of reliably administering the precise dose of amalgam contained within the barrel 3. This control of amalgam application is extremely important to a dentist and cannot be minimized. This is one reason why dentists who are trained with syringe-type applicators never adapt or switch to using lever-type applicators as illustrated herein and vice versa.

While the present invention has been illustrated with a lever-actuated 6 applicator 10 herein, it is also contemplated to practice the present invention with a syringe-type actuated applicator as disclosed, e.g., in U.S. Pat. No. 2,903,794 to Carfagni, in which case the plunger 28 and the outer barrel-like tip 12 are constructed as described supra. Furthermore, although the respective figures illustrate the barrel 3 formed of plastic and the plunger 1 of coated 9 metal 8, it is within the contemplation of the present invention to form the plunger 1, or at least the tip portion 2 thereof, entirely of plastic material and the barrel 3 of coated metal/metallic material. Moreover, both the plunger 2 and barrel 3 can be formed entirely of certain plastic material, or alternatively, both the plunger 2 and barrel 3 can both be formed of metal/metallic material coated with certain material, within the contemplation of the present invention.

The plastic used to fabricate the barrel 3 should be approved by the Food and Drug Administration (F.D.A.) as Food compliant. Suitable plastics are enumerated, e.g., at 21 C.F.R. §177(a) pp. 204–205, the contents of which are incorporated by reference herein. More particularly, the plastic can be suitable homopolymers, copolymers or terpolymers any of acceptable polyethylenes, polypropylenes, polymethacrylates, derivatives of any of the foregoing, or mixtures thereof. Especially preferred plastics include:

DELRIN, a crystalline thermoplastic polyacetal resin, available from E.I. Du Pont de Nemours & Co., Inc., Wilmington, Del.;

TEFLON, (polytetrafluoroethylene), also available from Du Pont;

RADEL, a polysulfone resin available from Union Carbide Corp., Ridgefield, Conn.;

NYLON (polyamide) also available from Du Pont;

NYLON 6 (linear polymer obtained by polymerizing ε-caprolactam), also available from Du Pont; and ULTEM (polyetherimide) available from General Electric Co., Fairfield, Conn.

The plunger 1 itself, and the handle 5, can both be manufactured from a stainless steel substrate, e.g., from Stainless Steel 300 series available from Ulbrich Stainless, North Haven, Conn. Additionally, the plunger 1 is coated with a coating 9 as enumerated, e.g., in 21 C.F.R. §175.300 such as Teflon 959-203 (FDA compliant) available from Du Pont, Xylan 8110-1879 black (FDA compliant) a food grade version of a polytetrafluorethylene-based industrial coating available from Whitford Corporation, Frazer, Pa., and NEDOX synergistic coating (an electroless nickel coating with fluorocarbon impregnation) and titanium nitride coating, both available from General Magnaplate, Linden, N.J. All these coatings are F.D.A. compliant. Additionally, F.D.A. compliant chromium coating available as Medicos 2000 from the Electrolizing Corporation of Ohio, Cleveland, Ohio, and carbon-based coating available as Diamonex DLC from Diamonex Performance Products, Allentown, Pa., can be utilized in accordance with the present invention.

Conversely, the plunger 1 can be fabricated from any of the above-mentioned plastics while the barrel 3 can be fabricated from stainless steel or similar metal and coated with any of the above-enumerated coatings. Furthermore, instead of metallic material, the plunger 1 or barrel 3 can be manufactured from a ceramic base in turn coated with any of the above-enumerated coatings. One such suitable ceramic is available from Coors Ceramics, Golden, Colo.

The component manufactured from plastic can be injection molded while the component of metal or ceramic can be coated by being dipped in an appropriately heated bath of coating material 9. The bath of coating material 9 can be heated to appropriate temperature which liquefies the coating which will then solidify upon cooling. Additionally, the resulting components can be easily sterilized without danger of softening. For example, TEFLON can be heated to a temperature of about 500° F. without softening while DELRIN can be heated up to about 250° F. without softening. Additionally, Diamonex can be heated to a temperature range of 750–900° F. without softening, while Xylan can be heated to a temperature of about 500° F. without softening. An additional advantage provided by the inventive applicator is that the various components can be easily size-colored. Previously, dentists had to use small silicone bands around the end of a handle as size indicators. The present invention will eliminate need for using such bands which can become separated, by providing automatic color coding based upon size, i.e., different color plastic/coating can be used for different sizes. The combination of components as set forth herein possesses sufficient lubricity to prevent amalgam from adhering while at the same time, possessing sufficient hardness so that a dentist's control is not sacrificed and the overall applicator can be sterilized in an autoclave without damage.

In a preferred embodiment, a plunger tip 2 of Stainless Steel 302 and coated with Teflon, possesses a Knoop coating hardness (10 gram load) of about 20.5 $HK_{10}$ for an average of 5 readings with 0.081 inch test wire and about 17.2 $HK_{10}$ for an average of 5 readings with a 0.110 inch test wire (testing carried out according to ASTM E-384-89). Accordingly, a coated 9 plunger 1 in accordance with the present invention should possess a Knoop hardness $HK_{10}$ of about 15–21, preferably about 17–20. The plunger 1 preferably possesses a coating 9 hardness on the Shore A scale of approximately 95 to 100. The plunger tip, in particular, possesses a coating hardness softer and below the Rockwell C hardness scale.

As a result of the inventive combination of plunger 1 and barrel 3, the inventive applicator 10 can be manufactured with fairly tight tolerances without any danger of abrading or damaging the inner surface of barrel 3 or outer surface and tip 2 of plunger 1. At the same time, provision of such tight tolerances helps prevent amalgam residue from "crawling up" the barrel 3 inner surface and then adhering to the barrel 3 and/or plunger 1. For example, the inner diameter of plastic barrel 3 can be approximately 0.080 inches while the outer diameter of coated plunger 1 can be about 0.0795 inches, providing a tolerance range radius of about 0.0005 inches, comparatively small when compared to prior art dental applicators. In this regard, the thickness of the coating is approximately 0.0004–0.0008 inches, with a thickness of about 0.0005 inches being most preferred. However, various sizes of barrel and plunger, e.g., four various complementary sizes, are provided for in the present invention.

The components forming the lever 6, barrel 3 and plunger 1 of the inventive applicator 10 can be permanently affixed to a handle 5 as with prior art applicators. However, it is also possible within the present invention to provide a dental applicator 10 in which the lever 6, barrel 3 and plunger 1 components are removably mounted upon the handle 3 as illustrated, e.g., in FIGS. 1–4. More particularly, as illustrated in FIGS. 1–4, a base 4 is provided with a channel 11 shaped to receive an extended straight end 12 of hook-shaped plunger 1 which is secured therein by a rivet or nut bolt 13. The leaf spring 7 is concentrically mounted about a neck of the base 4 by means of a collar 14, with an opposite end 15 of spring 7 hooking onto an opening 16 in lever 6 as illustrated in FIGS. 2 and 3. The barrel 3 itself comprises a recess 17 between two adjacent collars and into which a curved end 18 of lever 6 is received as illustrated.

The various component parts forming the pivotally mounted lever 6 and barrel 3 about the plunger, are assembled upon base 4 in the manner illustrated in FIG. 4. The base 4, which can be constructed of stainless steel or other metal/metallic material, ceramic material or of plastic material similar to barrel 3 described supra, is removably mounted in the interior hollow of handle 5 as illustrated in FIGS. 2–4. More particularly, a diametrical bar 20 is mounted across the interior hollow 19 of handle 5 as illustrated; base 4 terminates in an end shaped as a prong 21 and defining a recess 22 substantially complementary to bar 20.

The base 4 is also provided with an extension 23 upon which prong 21 is formed and which comprises an outer diameter substantially complementary to the interior diameter of handle 5. Collar 24 of base 4 is substantially equal in diameter to the outer diameter of handle 5. Therefore, when the base 4 and handle 5 are coupled together in the direction shown in FIG. 4, a force fit or snap fit is created so that base 4 together with all coupled components of the lever-actuated barrel and plunger mechanism are securely and reliably retained upon handle 5 as shown in FIG. 5. At the same time, base 4 and handle 5 can be easily uncoupled from one another by simple movement in opposite directions away from one another as shown in FIG. 5.

Figure 6:
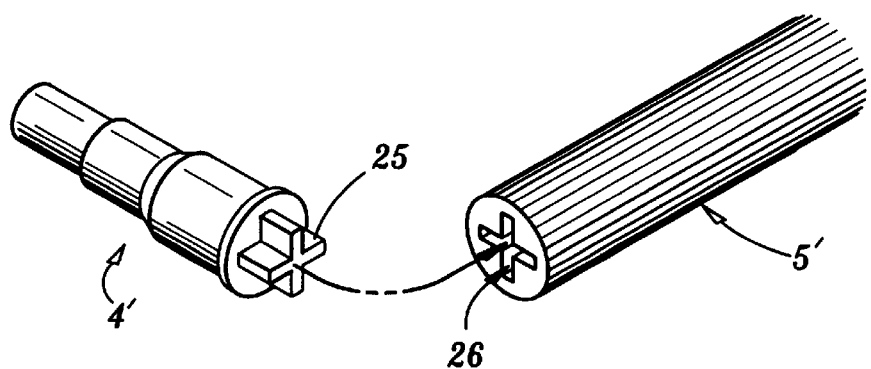
FIG. 6 is a schematic perspective view, similar to FIG. 5, and illustrating assembly of another embodiment of the dental applicator in accordance with the present invention.
Figure 7:
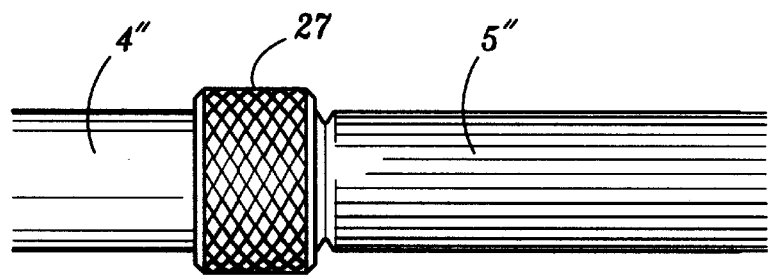
FIG. 7 is an elevational view illustrating the pertinent portion of an assembled, coupled dental applicator in accordance with the present invention.
Figure 8:
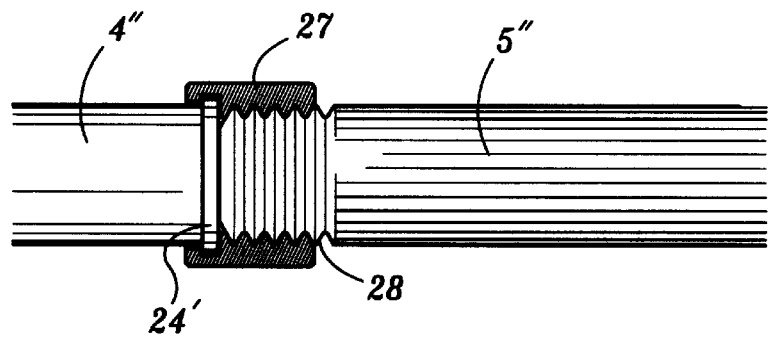
FIG. 8 is a sectional view of FIG. 7.

FIGS. 6–11 illustrate various alternative embodiments for coupling base 4 and handle 5 together. In FIG. 6, base 4' and handle 5' are provided with complementary male and female members in the shape of a cross. The other features of handle 5' and base 4' remain identical to handle 5 and base 4 shown in FIGS. 1–5. In the embodiment illustrated in FIGS. 7 and 8, an end of handle 5' is provided with external threads 28 while a nut 27 comprising complementary internal threads is mounted upon collar 24' of base 4". This coupling feature shown in FIGS. 7 and 8 can be combined with any of the other coupling features shown in FIGS. 1-6 described supra or FIGS. 9–11 described infra.

Figure 9:
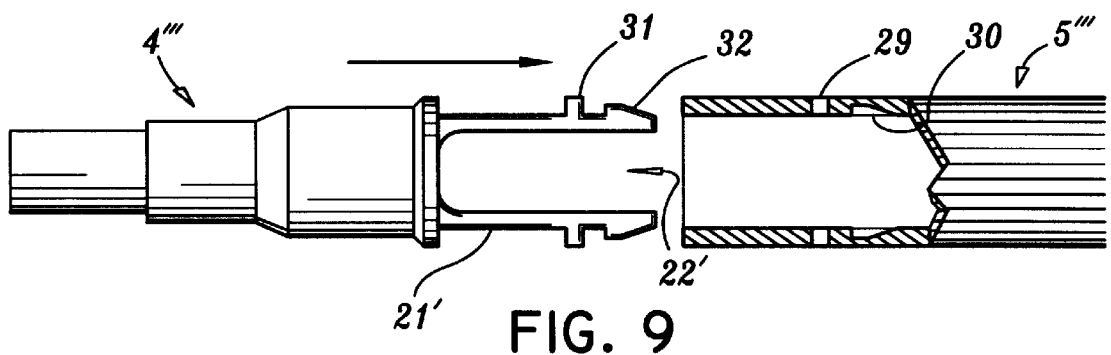
FIGS. 9–11 are schematic views illustrating coupling and assembly of other embodiments of a dental applicator in accordance with the present invention.
Figure 10:
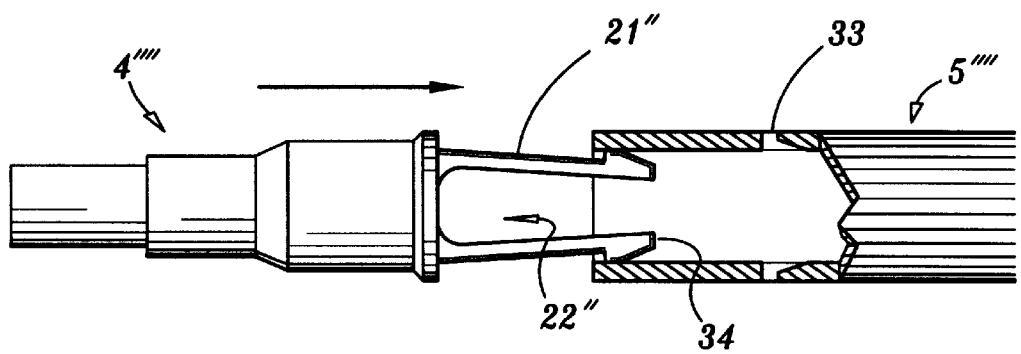
Figure 11:
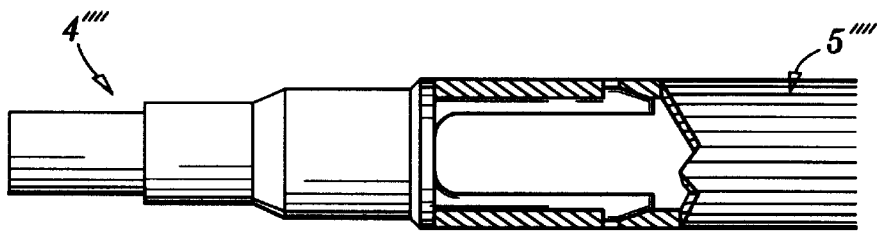

In the embodiment shown in FIG. 9, prong 21 has been manufactured of resilient material comprising projections 31 and 32 shaped to respectively seat in annular grooves 29 and 30 of handle 5'''. In FIGS. 10 and 11, prong 21" has been provided with slightly altered projections 34 (also resiliently biased) and with handle 5''' provided with differentially-shaped annular grooves 33 to accept projections 34. The operation of coupling the embodiment shown in FIG. 9 is identical to the coupling illustrated in FIGS. 10 and 11; to uncouple either of these two applicator tips, a sharp instrument is inserted into grooves 33 (FIG. 11) or 29 to bias prongs 21" or 21' together and thereby permit the respective base and handle to be moved apart.

The present invention can be applied to an amalgam dispenser having dispensing rods at opposite ends as shown, e.g., in U.S. Pat. No. 4,306,864 to Law et al.

The preceding description of the present invention is merely exemplary and is not intended to limit the scope thereof.

We claim:

1. A dental applicator, comprising the combination of:

a barrel, a plunger arranged to reciprocate into and out of said barrel, wherein said barrel is fabricated from plastic and said plunger is fabricated from a ceramic, metal, or metallic material provided with a coating thereon, additionally comprising a lever, with said barrel mounted on an end of said lever, a base to which said plunger is secured at one end thereof and upon which said lever is pivotally mounted, said base structured and arranged to be secured to a handle at an opposite end thereof, a spring concentrically mounted about said base at one end thereof, an opposite end of said spring coupled to said lever having said barrel mounted at said one end thereof and with a finger piece at an opposite end of said lever which is arranged to be depressed towards said base, with said spring arranged to bias said lever and barrel into a normally extended position over said plunger and when said finger piece is depressed, said lever and barrel retract upwardly away from a tip of said plunger, wherein said base is structured and arranged to be detachably secured to, retained by and removable from said handle, said handle is at least partially hollow and comprises a bar diametrically mounted thereacross, and said base comprises an end portion opposite said plunger and having an outer diameter substantially complementary to an inner diameter of said handle and a curved recess arranged to receive said bar when said base and handle are coupled together, whereby said base with lever, barrel and plunger mounted thereon can be coupled with said handle by a snap fit, and can be uncoupled from said handle by a simple sharp tug on said base in a direction away from said bar.

2. The applicator of claim 1, wherein said plunger possesses a coating hardness softer and below the Rockwell C hardness scale.

3. The applicator of claim 2, wherein said plunger possess a coating hardness on the Shore A scale of approximately 95 to 100.

4. The applicator of claim 1, wherein said plastic is selected from the group consisting of crystalline thermoplastic polyacetal resin, polytetrafluoroethylene, polysulfone resin, polyamide, linear polyamide obtained by polymerizing ε-caprolactam, polyetherimide and mixtures thereof.

5. The applicator of claim 1, wherein the metal is stainless steel.

6. The applicator of claim 5, wherein the coating is polytetrafluoroethylene and the plastic is polysulfone resin.

7. The applicator of claim 1, wherein the coating is selected from the group consisting of polytetrafluoroethylene, electroless nickel, titanium nitride, chromium-based and carbon-based coating and mixtures thereof.

8. The applicator of claim 1, wherein said base additionally comprises a channel for receiving said plunger, said plunger is secured to said base with a rivet or nut and bolt, and said spring comprises a collar concentrically mounted upon said base.

9. The applicator of claim 1, wherein said base is formed of plastic or metal.

10. The applicator of claim 1, wherein said plastic is selected from the group consisting of crystalline thermoplastic polyacetal resin, polytetrafluorethylene, polysulfone resin, polyamide, linear polyamide obtained by polymerizing ε-caprolactam, polyetheramide and mixtures thereof;

the metal is stainless steel, and the coating is selected from the group consisting from polytetrafluoroethylene, electroless nickel, titanium nitride, chromium-based and carbon-based coating and mixtures thereof.

11. The applicator of claim 1, which is structured and arranged to maintain touch and control for administration of amalgam or condensed resin by a dentist, thereby ensuring reliable control for administration of the amalgam or resin by a dentist while facilitating cleaning of the applicator.

12. The applicator of claim 11, which is structured and arranged to prevent metallic streaking upon condensed resin being dispensed therefrom.

13. The applicator of claim 11 wherein said plunger is entirely coated to prevent unwanted adherence of amalgam or condensed resin and ensure ejection of the entire amalgam or resin contains upon a dispensing of the same by the dentist.

14. The applicator of claim 11, wherein said barrel and plunger are arranged to fit together with tight tolerance to prevent amalgam from sliding up an inner surface of said barrel and adhering to said barrel and plunger, upon dispensing.

15. The applicator of claim 14, having a tolerance range radius between said barrel and plunger of approximately 0.0005 inches, with a thickness of said coating being approximately 0.0004–0.0008 inches.

16. A dental applicator, comprising the combination of:

a barrel, a plunger arranged to reciprocate into and out of said barrel, wherein said barrel is fabricated from plastic and said plunger is fabricated from a ceramic, metal, or metallic material provided with a coating thereon.

additionally comprising a lever, with said barrel mounted on an end of said lever, a base to which said plunger is secured to at one end thereof and upon which said lever is pivotally mounted, said base structured and arranged to be secured to a handle at an opposite end thereof, a spring concentrically mounted about said base at one end thereof, an opposite end of said spring coupled to said lever having said barrel mounted at said one end thereof and with a finger piece at an opposite end of said lever which is arranged to be depressed toward said base, with said spring arranged to bias said lever and barrel into a normally extended position over said plunger and when said finger piece is depressed said lever and barrel retract upwardly and away from a tip of said plunger, wherein said base is structured and arranged to be detachably secured to, retained by and removable from said handle, said base and handle comprise:
respective ends arranged to be coupled to one another, and
said ends comprising complementary male and female members in the shape of a cross,
whereby said base and handle can be coupled together by snap fitting with easy removal.

17. The applicator of claim 16, wherein said male member is provided on an end of said base and said female member is provided on an end of said handle.

18. The applicator of claim 16, wherein, one of said base and handle comprises external threads, the other of said base and handle comprises an outwardly extending flange, and a nut comprising internal threads is mounted upon said flange and arranged to be screwed onto said external threads, whereby said base and handle can be coupled and secured together.

19. The applicator of claim 18, wherein said base is provided with said male member and said flange, and said handle is provided with said external threads and with said female member provided therein.

20. A dental applicator, comprising the combination of:
a barrel, a plunger arranged to reciprocate into and out of said barrel, wherein said barrel is fabricated from plastic and said plunger is fabricated from a ceramic, metal, or metallic material provided with a coating thereon, additionally comprising a lever, with said barrel mounted on an end of said lever, a base to which said plunger is secured at one end thereof and upon which said lever is pivotally mounted, said base structured and arranged to be secured to a handle at an opposite end thereof, a spring concentrically mounted about said base at one end thereof, an opposite end of said spring coupled to said lever having said barrel mounted at said one end thereof and with a finger piece at an opposite end of said lever which is arranged to be depressed toward said base, with said spring arranged to bias said lever and barrel into a normally extended position over said plunger and when said finger piece is depressed said lever and barrel retract upwardly and away from a tip of said plunger, wherein said base is structured and arranged to be detachably secured to, retained by and removable from said handle, said handle is at least partially hollow at one end thereof, said base comprises a pair of resilient spring-like members mounted upon an end thereof opposite said plunger, with each said spring-like member comprising a lateral projection thereon, said handle comprising a pair of bores extending therethrough from an inner surface to an outer surface thereof in the hollow portion and arranged to receive the lateral projections of said spring-like members when inserted therein, whereby said base and handle can be coupled together by pressing said spring-like member towards one another, and inserting the same into said hollow end of said handle and causing said lateral projections to be received in said respective bores so that said spring-like members can spring outwardly away from one another to secure said base and handle together, and said base and handle can be decoupled by depressing said lateral projections seated in said respective bores towards one another and simultaneously pulling said base and handle apart.

21. The applicator of claim 20, additionally comprising:

a second set of lateral projections on said spring-like member, and a pair of recesses on the inner surface of the hollow portion of said handle and arranged to receive said second set of lateral projections to additionally secure said base and handle together when said base and handle are coupled together.

* * * * *